United States Patent
Ogawa

(10) Patent No.: US 6,686,590 B2
(45) Date of Patent: Feb. 3, 2004

(54) LOW-VACUUM SCANNING ELECTRON MICROSCOPE

(75) Inventor: Kouji Ogawa, Tokyo (JP)

(73) Assignees: JEOL Ltd., Tokyo (JP); JEOL Technics Ltd., Tokyo (JP)

( * ) Notice: Subject to any disclaimer, the term of this patent is extended or adjusted under 35 U.S.C. 154(b) by 0 days.

(21) Appl. No.: 10/105,806

(22) Filed: Mar. 25, 2002

(65) Prior Publication Data

US 2002/0166966 A1 Nov. 14, 2002

(30) Foreign Application Priority Data

Mar. 26, 2001 (JP) ............................ 2001-87629

(51) Int. Cl.7 ............................................. G01N 23/00
(52) U.S. Cl. ..................................................... 250/310
(58) Field of Search ................................ 250/306–307, 250/310–311, 396 R, 399, 427

(56) References Cited

U.S. PATENT DOCUMENTS 4,785,182 A   11/1988   Mancuso et al. ............ 250/310
5,677,531 A * 10/1997   Miyazaki .................... 250/310
6,365,898 B1 *  4/2002   Sudraud et al. ............. 250/310

FOREIGN PATENT DOCUMENTS

| GB | WO 87/05150 | * | 8/1987 | |
| JP | 2002-100316 | * | 5/2002 | .......... H01J/37/244 |
| WO | 8705150 | | 8/1987 | |
| WO | 9822971 | | 5/1998 | |

* cited by examiner

Primary Examiner—John R. Lee
Assistant Examiner—Christopher M. Kalivoda
(74) Attorney, Agent, or Firm—Webb Ziesenheim Logsdon Orkin & Hanson, P.C.

(57) ABSTRACT

There is disclosed a low-vacuum scanning electron microscope wherein a bias voltage is applied to a specimen. A primary electron beam is made to strike the specimen, producing secondary electrons which are accelerated by an electric field producing an electron avalanche effect. Positive ions traveling toward the specimen reach the specimen or specimen holder. Then, the electrons lose their electric charge and return to molecules. In this way, a scanned image corresponding to a secondary electron image can be obtained based on the specimen current.

9 Claims, 5 Drawing Sheets

LOW-VACUUM SCANNING ELECTRON MICROSCOPE

BACKGROUND OF THE INVENTION

1. Field of the Invention

The present invention relates to a low-vacuum scanning electron microscope that can maintain the interior of a specimen chamber at a low vacuum, can prevent charging of a specimen, and permits observation of a specimen in its intact state even if it contains moisture.

2. Description of Related Art

In scanning electron microscopy, an electron beam is sharply focused onto a specimen, and a desired area on the specimen is scanned with the electron beam. As the electron beam hits the specimen, secondary electrons and backscattered electrons are ejected. These electrons are detected, and the resulting detection signal is supplied to a cathode-ray tube synchronized with the scanning of the primary electron beam. In this way, a scanned image of the specimen is displayed.

The essential structure of this scanning electron microscope is described by referring to FIG. 1. An electron gun (not shown) for emitting and accelerating an electron beam, condenser lenses (not shown), and other components are mounted above an objective lens 1. The primary electron beam 2 is focused sharply by the condenser lenses and objective lens 1 and directed at a specimen 3. Scan coils (not shown) for scanning the primary electron beam 2 over the specimen in two directions are disposed above or inside the objective lens 1.

As the electron beam 2 hits the specimen 3, secondary electrons are produced. These secondary electrons are collected by a mesh-like collector 5. A voltage of about 300 V is applied to the collector from a power supply 4. The secondary electrons collected by the collector 5 are guided to a secondary electron detector 7. This detector 7 is composed of a corona ring 9 applied with a high voltage of about 10 kV from a corona ring power supply 8, a scintillator 10 on which secondary electrons accelerated by the corona ring 9 impinge, and a photomultiplier tube 11 for converting light from the scintillator into an electrical signal.

The secondary electron signal from the secondary electron detector 7 is supplied as a brightness-modulating signal to a CRT via an amplifier (not shown) and via a signal-processing circuit (not shown) for adjusting the brightness and the contrast. The CRT is synchronized with the scanning of the primary electron beam. As a result, a secondary electron (SE) scanned image of a certain two-dimensional area on the specimen is displayed on the viewing screen of the CRT.

Where the specimen 3 is an insulator or contains moisture, it is customary to set low the degree of vacuum in the specimen chamber where the specimen 3 is placed. However, if the degree of vacuum inside the specimen chamber is lowered, electric discharging occurs because a high voltage is applied to the corona ring 9. Therefore, the secondary electron detector 7 cannot be used in a low vacuum. Consequently, under a low-vacuum condition, a backscattered electron detector to which high voltage is not applied is normally used to perform backscattered electron imaging.

Although a backscattered electron image contains a large amount of information about the composition of the specimen, the amount of information regarding the topography of the surface is small compared with a secondary electron image. For this reason, it has been difficult to image the three-dimensional topography of the specimen surface.

Accordingly, an absorption current detection method can be used as a method of obtaining an image similar to a secondary electron image even at a low vacuum. As a primary electron beam strikes a specimen, secondary electrons and backscattered electrons are ejected from the specimen. A feeble absorption current flowing through the specimen is measured. An image is created from variations in the magnitude of the current.

FIG. 2 shows a specific structure for implementing this detection method. An electrical current absorbed into the specimen 3 is measured by a specimen absorption current-measuring instrument 15. The measured absorption current is amplified by a current amplifier circuit 16 and is supplied to the CRT (not shown). Since the absorption current is far weaker than the incident current, introduction of noise is unavoidable. Therefore, it is difficult to obtain an image at a higher resolution unless the incident current is increased extremely.

SUMMARY OF THE INVENTION

It is an object of the present invention to provide a low-vacuum scanning electron microscope capable of efficiently obtaining an image similar to a secondary electron image even at a low degree of vacuum.

A low-vacuum scanning electron microscope, according to a first embodiment of the present invention, comprises: an electron gun for producing and accelerating an electron beam; condenser lenses for focusing the electron beam onto a specimen placed within a specimen chamber in a low vacuum, the specimen being maintained at a potential; scanning means for scanning the electron beam over the specimen in two dimensions; voltage generation means for setting the potential of the specimen such that the specimen is at a negative potential with respect to the specimen chamber; detection means for detecting an electric current flowing through the specimen and/or an electric current flowing through a specimen holder holding the specimen thereon; and means for obtaining a scanned image of the specimen based on an output signal from the current detection means. The voltage generation means sets the potential of the specimen based on information about the pressure inside the specimen chamber and on information about the distance between the specimen and the condenser lenses.

A low-pressure scanning electron microscope, in accordance with a second embodiment of the present invention, comprises: an electron gun for producing and accelerating an electron beam; condenser lenses for focusing the electron beam onto a specimen placed within a specimen chamber in a low vacuum; scanning means for scanning the electron beam over the specimen in two dimensions; an electrode placed above the specimen; voltage generation means for applying a voltage between the specimen and the electrode to accelerate secondary electrons toward the electrode, the secondary electrons being emitted from the specimen by electron beam irradiation; current detection means for detecting an electric current flowing through the specimen and/or an electric current flowing through a specimen holder holding the specimen thereon; and means for obtaining a scanned image of the specimen based on an output signal from the current detection means. The voltage generation means controls the voltage applied between the specimen and the electrode based on information about the pressure inside the specimen chamber and on information about the distance between the specimen and the condenser lenses.

Other objects and features of the invention will appear in the course of the description thereof, which follows.

DESCRIPTION OF THE PREFERRED EMBODIMENTS

Figure 1:
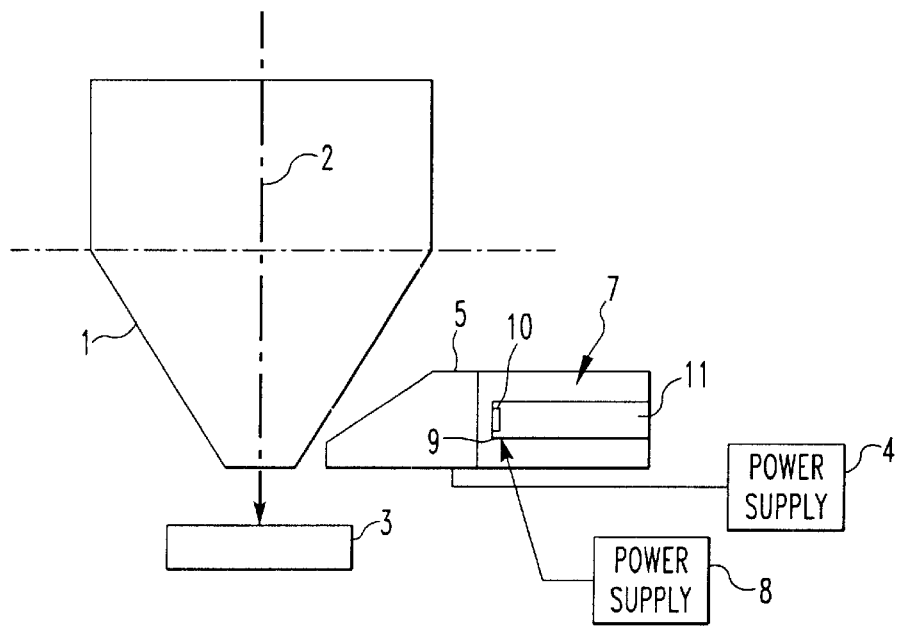
FIG. 1 is a schematic diagram of one conventional scanning electron microscope.
Figure 2:
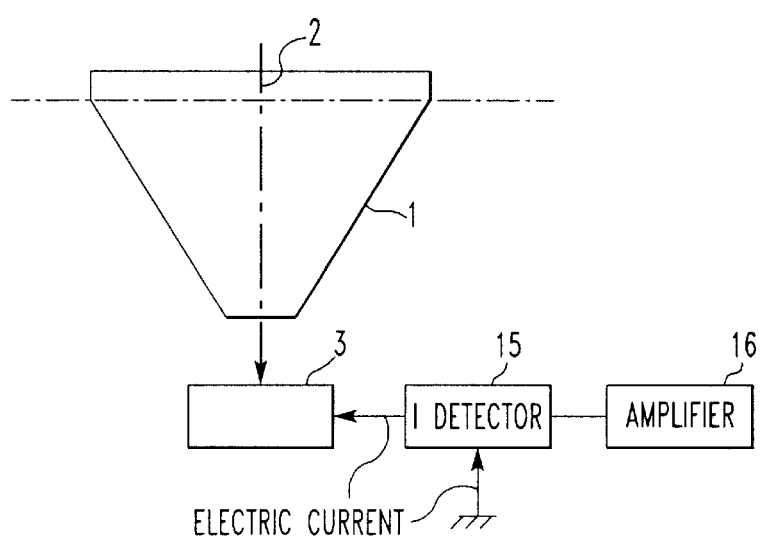
FIG. 2 is a schematic diagram of another conventional scanning electron microscope.
Figure 3:
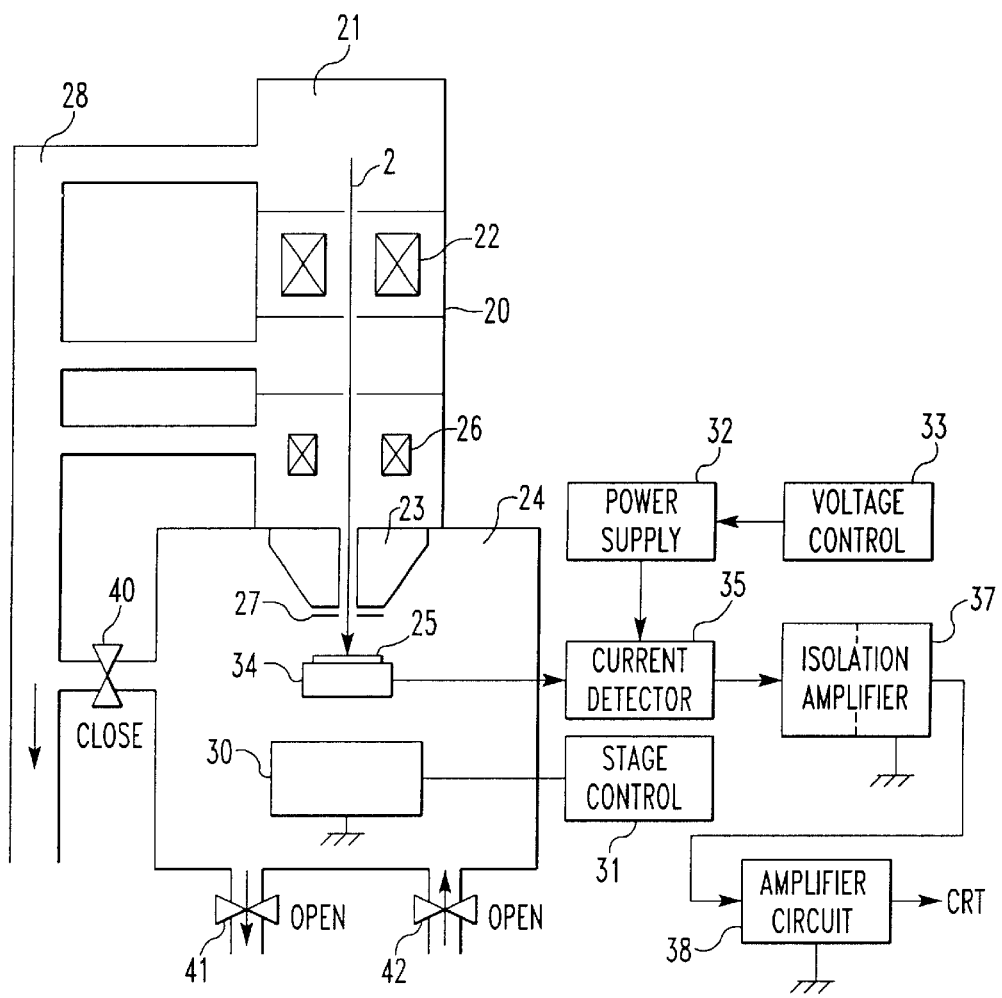
FIG. 3 is a schematic diagram of a scanning electron microscope according to the present invention.

Preferred embodiments of the present invention are hereinafter described with reference to the accompanying drawings. FIG. 3 shows one example of a low-vacuum scanning electron microscope according to the present invention. This microscope has a microscope column 20. An electron gun chamber 21 is disposed in an upper part of the column 20. An electron gun, such as a thermionic gun or field emission gun, is mounted within the electron gun chamber 21.

A primary electron beam 2 generated and accelerated by the electron gun is sharply focused onto a specimen 25 by a system of condenser lenses composed of condenser lenses 22 and an objective lens 23, the specimen 25 being positioned within a specimen chamber 24. Scan coils 26 for deflecting the primary electron beam 2 are mounted over the objective lens 23. Scanning signals are supplied to the scan coils 26 from a scanning signal generator circuit (not shown) to raster-scan a desired area on the specimen 25 with the primary electron beam.

An aperture plate 27 having a minute opening is mounted at the bottom of the objective lens 23. The space extending from the electron gun chamber 21 to the inside of the objective lens 23 is partitioned from the inside of the specimen chamber 24 by the aperture plate 27. Therefore, the electron gun chamber 21 and the space over the objective lens 23 are evacuated to a high vacuum by a diffusion pump or the like via an exhaust pipe 28, while the inside of the specimen chamber 24 can be maintained at a low vacuum.

Three valves 40, 41, and 42 are mounted in the specimen chamber 24. The valve 40 is used for connection with the exhaust pipe 28. When the scanning electron microscope is used at a low vacuum, this valve is closed. The valve 41 is connected with a rotary pump (not shown). The valve 42 is connected with a variable leak valve. The inside of the specimen chamber 24 is maintained at a desired pressure, or a desired degree of vacuum, by opening and closing the valves 41 and 42.

The specimen 25 is placed on a conductive specimen holder 34, which is placed on a specimen stage 30 and electrically insulated from it. The specimen stage 30 is moved in two directions (X- and Y-directions) within a plane and in a vertical direction in response to control signals from a stage control portion 31. A bias voltage is applied to the specimen holder 34 via a current-measuring circuit 35 from a specimen power supply 32. The bias voltage is determined by a voltage controller 33 that controls the specimen power supply 32. An isolation amplifier 37 insulatively takes out the output signal from the current-measuring circuit 35 indicative of the results of the measurement. The output signal from the current-measuring circuit 35 is supplied to a CRT (not shown) via an amplifier circuit 38 operating at ground potential. The operation of the instrument constructed in this way is described below.

Imaging of the specimen 25 in a low vacuum is first described. The electron beam passage area ranging from the electron gun chamber 21 to the inside of the objective lens 23 is evacuated to about $1 \times 10^{-3}$ Pa by a diffusion pump, for example, via the exhaust pipe 28. Meanwhile, the inside of the specimen chamber 24 is evacuated via the valve 41 by the rotary pump (not shown). Air or nitrogen gas is admitted into this specimen chamber 24 via the valve 42. Thus, the inside of the specimen chamber 24 is maintained at a low vacuum of the order of 10 to 300 Pa.

After the inside of the microscope column 20 and specimen chamber 24 has reached a desired degree of vacuum, a primary electron beam 2 is produced and accelerated by the electron gun inside the electron gun chamber 21. The primary electron beam 2 is sharply focused onto the specimen 25 by the condenser lenses 22 and objective lens 23. The primary electron beam 2 is scanned over the specimen surface in two dimensions by the scan coils 26. As the primary electron beam 2 hits the specimen 25, secondary electrons are ejected from it.

Figure 4:
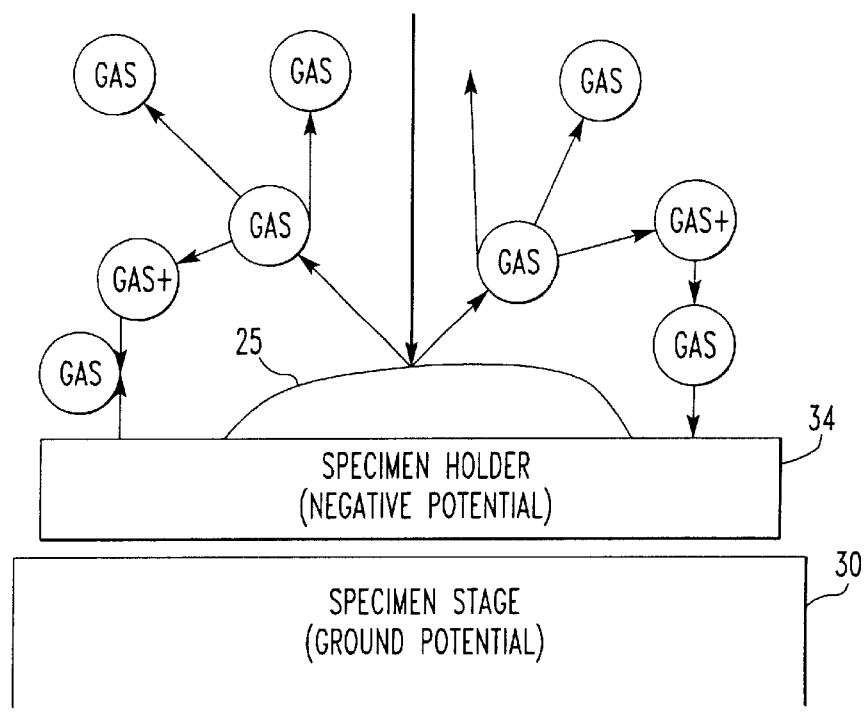
FIG. 4 is a diagram illustrating the manner in which gas molecules are ionized by secondary electrons.

FIG. 4 illustrates the behavior (i.e., ionization of gas molecules) of the secondary electrons produced from the specimen 25. A negative bias voltage of −300 V, for example, is applied to the specimen 25 (specimen holder 34) from the specimen power supply 32, while the specimen chamber 24 and objective lens 23 are at ground potential. Therefore, an electric field is produced around the specimen 25. The secondary electrons produced at the specimen surface are immediately moved away from the specimen surface by the electric field and accelerated toward the objective lens 23 or specimen chamber wall. Energy sufficient to ionize the surrounding gas molecules is imparted to the secondary electrons by the electric field. The secondary electrons collide against the gas molecules around the specimen 25 and ionize them.

Of ions and electrons produced in this way, negative ions and electrons are accelerated away from the specimen 25 by the aforementioned electric field. Meanwhile, positive ions are accelerated toward the specimen 25. These ions collide against surrounding gas molecules, resulting in further ions and electrons. That is, an electron avalanche phenomenon is produced. Positive ions arriving at the specimen 25 (specimen holder 34) accept electrons from the specimen 25 (specimen holder 34) and return to neutral molecules. A specimen current owing to the flow of electric charge occurring at this time is detected by the current-measuring circuit 35 and isolation amplifier 37. The detected specimen current corresponds to the number of the secondary electrons originally produced from the specimen surface and multiplied.

The process of the aforementioned electron avalanche varies depending on the pressure around the specimen 25 and on the kind of gas. If the electric field is too intense, the process easily shifts to electric discharging. If the field is too weak, sufficient multiplication cannot be obtained. Where the bias voltage is not varied, if the working distance between the specimen 25 and the lower end of the objective lens 23 is varied, the electric field varies, changing the electron avalanche phenomenon. Accordingly, it is difficult to stabilize the electron avalanche phenomenon at all times.

We have confirmed, however, that with respect to a gas pressure and an electric field strength which cause an ideal electron avalanche phenomenon, if one of the pressure and field strength is determined, then the other is almost uniquely determined. Accordingly, the present invention provides a function of setting an optimum bias voltage by the pressure inside the specimen chamber 24 and the working distance. Consequently, an electron avalanche phenomenon can be caused ideally at all times regardless of the state of the instrument. A specimen current corresponding to the amount of secondary electrons emanating from the specimen 25 can be detected efficiently.

Another advantage of the application of a bias voltage to the specimen holder 34 (specimen) is that convergence of ions produced around the specimen 25 is assured, as well as acceleration of the secondary electrons. The application of the bias voltage to the specimen 25 can induce an electron avalanche phenomenon around the specimen 25 where the electric field strength is especially intense. The bias voltage assures that positive ions produced by the electron avalanche phenomenon are conveyed toward the specimen 25 without being affected by ground potential existing in numerous locations around the specimen 25, such as the specimen chamber wall and various members installed in the chamber.

Generally, in the case of a nonconducting specimen, the absorption current into the specimen 25 is reduced by the resistance of the specimen 25 itself and, therefore, it is difficult to measure the current. In this case, however, if the specimen 25 is dielectric, the negative voltage applied to the specimen holder 34 induces dielectric polarization in the specimen 25. This negatively charges the specimen surface on the side of the objective lens 23. If the specimen 25 is so small that it is entirely encased in the electric field produced around the specimen holder 34, the electric field owing to the dielectric polarization in the specimen 25 is intensified by the electric field produced around the specimen holder 34. Therefore, the aforementioned positive ions generated by collision of the secondary electrons with gas molecules are accelerated toward the specimen 25. On reaching the specimen 25 (specimen holder 34), the positive ions receive electrons from the specimen 25 (specimen holder 34) and return to neutral molecules. Flow of electric charge resulting at this time creates an electric current through the specimen holder 34. The current is detected by the current-measuring circuit 35 in the same way as in the above-described process.

In this way, in the present invention, if the specimen 25 is a nonconducting specimen, a current signal can be effectively obtained by making use of an electron avalanche phenomenon producing an amount of signal that is several times as much as a current signal produced by secondary electrons, which, in turn, are generated by a primary electron beam. Hence, the effect of the decrease in the absorption current can be almost neglected.

Figure 5:
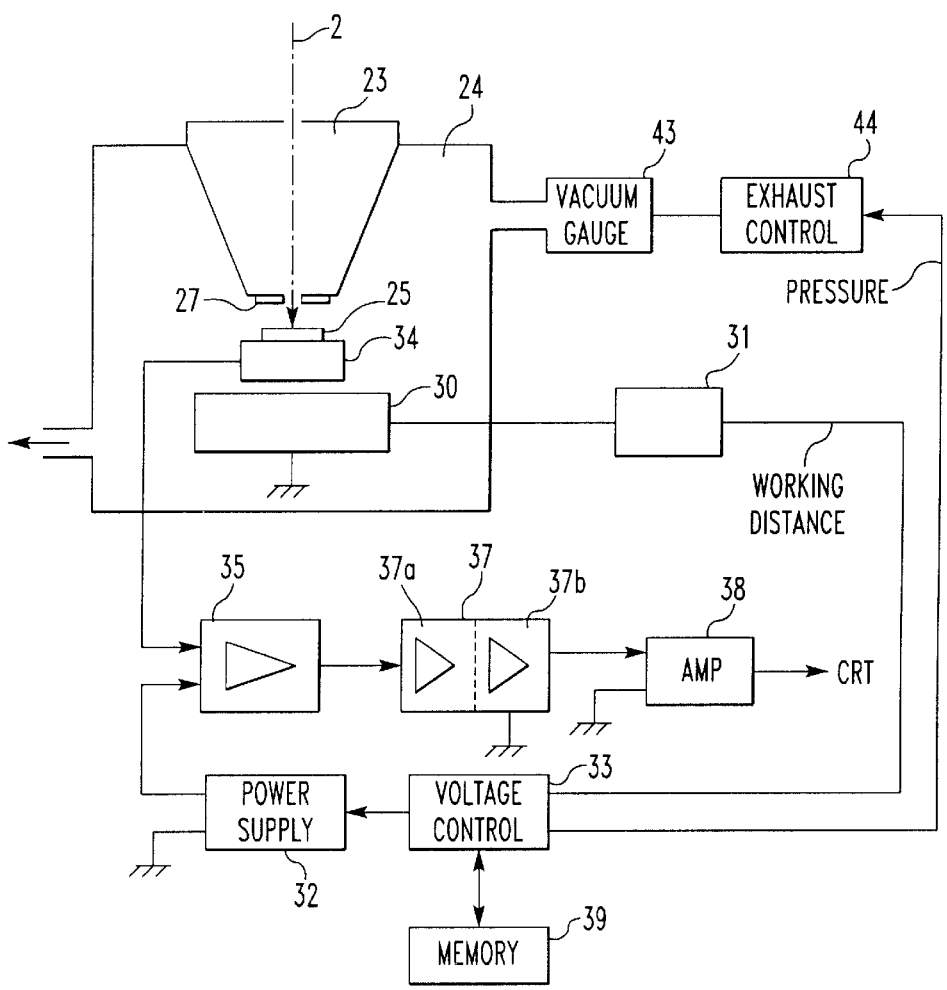
FIG. 5 is a diagram showing one example of a circuit for detecting an absorption current.

FIG. 5 shows a circuit configuration for detecting the specimen current. An electrical current absorbed into the specimen 25 and specimen holder 34 is detected by the current-measuring circuit 35 and supplied to the isolation amplifier 37. This amplifier 37 is made up of an input stage of amplifier 37a and an output stage of amplifier 37b, which are electrically isolated from each other. The output stage of amplifier 37b of the isolation amplifier 37 operates at ground potential and produces an output signal, which is amplified by the amplifier 38 and then supplied to the CRT (not shown). As a result, a scanned image owing to the specimen current is displayed on the CRT. As mentioned previously, a specimen current detected during the process of an electron avalanche phenomenon has a component proportional to the number of secondary electrons emitted from the specimen 25. Therefore, this scanned image is close in quality to a secondary electron image and well represents the topography of the specimen surface.

The specimen power supply 32 for generating the bias voltage is controlled by the voltage controller 33 to which signals indicating information about the present working distance and information about the pressure inside the specimen chamber 24 are supplied. Multiple values of optimum bias voltage producing an optimum electron avalanche effect and corresponding to multiple values of the pressure inside the specimen chamber 24 and multiple values of the distance are stored as a table in the memory 39. That is, the table consists of multiple sets of combinations of these values. The voltage controller 33 reads data about an optimum bias voltage from the table according to information about the entered, present working distance and the pressure inside the specimen chamber 24 and sends the data to the specimen power supply 32. This power supply 32 applies such a bias voltage to the specimen 25 via the specimen holder 34 as to produce an optimum electron avalanche phenomenon.

The aforementioned information about the pressure inside the specimen chamber 24 is obtained by a vacuum gauge 43 mounted to the specimen chamber 24. The obtained information is sent to the voltage controller 33 via an exhaust system control portion 44. The information about the working distance is sent to the voltage controller 33 from a stage control portion 31 that controls the specimen stage 30.

Figure 6:
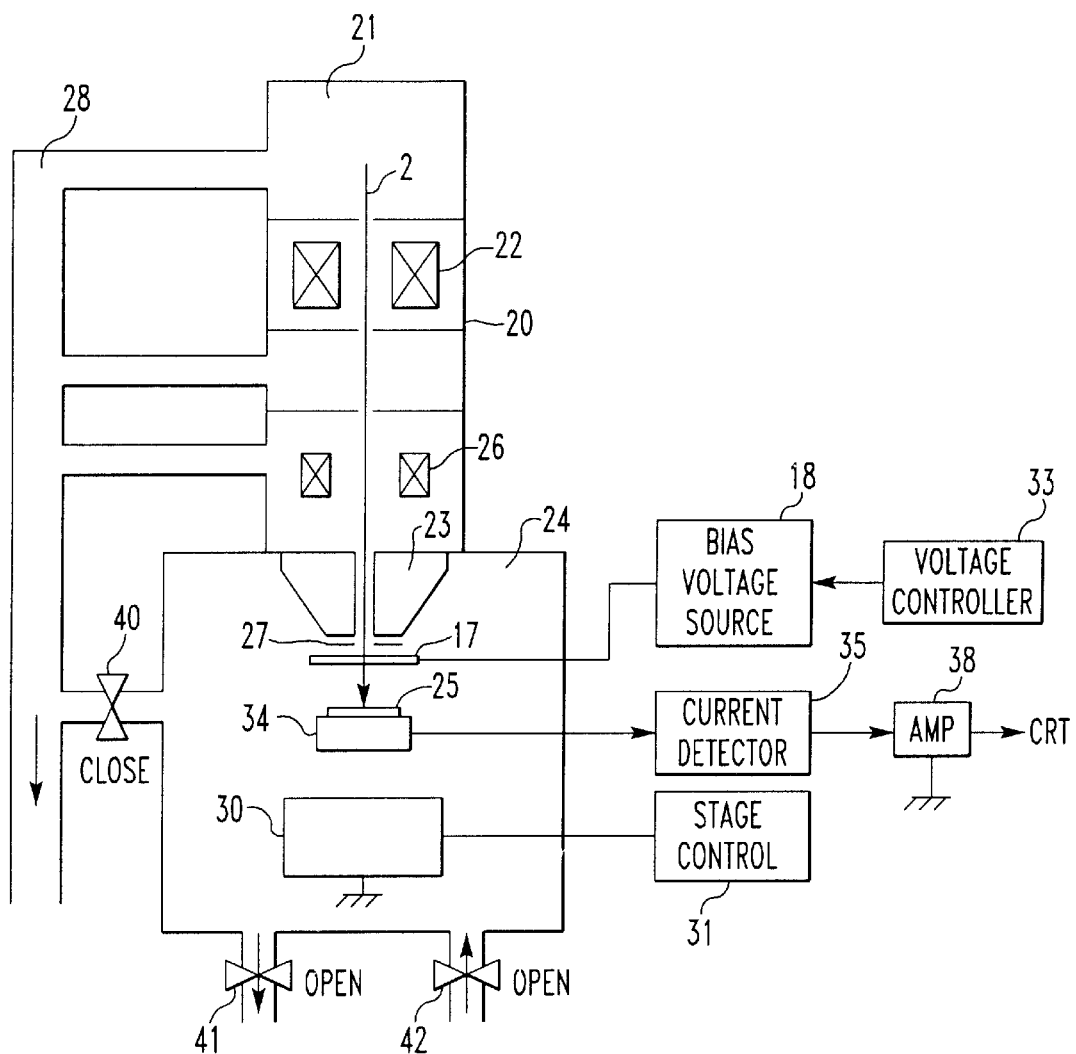
FIG. 6 is a diagram similar to FIG. 3, but showing another embodiment of the present invention.

FIG. 6 shows another embodiment of the present invention. Note that those components of FIG. 6, which are the same as their respective counterparts shown in FIG. 3, are indicated by the same reference numerals as in FIG. 3.

In FIG. 6, an annular electrode 17 is disposed under the objective lens 23. A bias voltage is applied to the electrode 17 from a bias voltage source 18. In this case, the specimen 25 is grounded or a negative voltage is applied to the specimen holder 34 to place a negative potential on the specimen 25. Meanwhile, the bias voltage source 18 places the electrode 17 at a positive potential with respect to the specimen 25. An electric field produced between the specimen 25 and the electrode 17 accelerates secondary electrons and other electrons ejected from the specimen 25 toward the electrode 17. During the movement, they collide against surrounding gas molecules, giving rise to an electron avalanche phenomenon. Resulting positive ions move toward the specimen 25 and which are detected as a specimen current.

The voltage controller 33 and other components for producing an optimum bias voltage from the bias voltage according to the pressure inside the specimen chamber 24 and the working distance are identical in structure and operation with those described already in connection with FIG. 3.

While the preferred embodiments of the present invention have been described thus far, the invention is not limited thereto. For instance, data about the height of the specimen 25 above the specimen stage 30 may be used as information about the working distance. The information may also be data found from an excitation current value that brings the objective lens 23 in focus. Furthermore, in the above embodiments, the optimum bias voltage is found from information about the working distance and from information about the pressure inside the specimen chamber 24 by the voltage controller 33. The function of the voltage controller 33 may be given to a central-processing unit (not shown) that controls the whole scanning electron microscope.

As described thus far, in the first embodiment of the present invention, a voltage is applied to a specimen 25, and secondary electrons ejected from the specimen 25 are accelerated by the produced electric field. Thus, gas molecules are ionized. The ionized gas molecules and electrons are accelerated by the electric field and collide against other gas molecules, thus ionizing them. This causes an electron avalanche phenomenon. Positive ions are attracted toward the specimen 25 and absorbed into it. A secondary electron image is displayed based on the current absorbed into the specimen 25. As a result, secondary electrons and surrounding gas molecules can produce an electron avalanche phenomenon around the specimen 25. In consequence, the multiplied secondary electrons can be detected, amplified, and imaged as a specimen absorption current.

The application of a voltage to the specimen or to its vicinity prevents a situation such that ions move toward surrounding ground potential (0 V) regardless of the working distance. This assures that the ions are collected around the specimen. Hence, the absorption current can be obtained more efficiently.

Furthermore, the application of the voltage to the specimen or to its vicinity promotes ejection of electrons from around the specimen. As a result, the absorption current can be obtained with improved efficiency.

Having thus described my invention with the detail and particularity required by the Patent Laws, what is desired protected by Letters Patent is set forth in the following claims.

The invention claimed is:

1. A low-vacuum scanning electron microscope comprising:
   an electron gun for producing and accelerating an electron beam;
   condenser lenses for focusing said electron beam onto a specimen placed within a specimen chamber in a low vacuum, said specimen being at a potential, said specimen being at a distance from said condenser lenses;
   scanning means for scanning said electron beam over said specimen in two directions;
   voltage generation means for setting the potential of said specimen such that said specimen is at a negative potential with respect to said specimen chamber;
   detection means for detecting an electric current flowing through said specimen and/or an electric current flowing through a specimen holder holding said specimen thereon; and
   means for obtaining a scanned image of the specimen based on an output signal from said current detection means,
   wherein said voltage generation means sets the potential of said specimen to promote an avalanche effect based on information about pressure inside said specimen chamber and on information about the distance between said specimen and said condenser lenses.

2. The low-vacuum scanning electron microscope of claim 1, wherein there is further provided a memory in which multiple values of optimum bias voltage corresponding to multiple values of the pressure inside the specimen chamber and multiple values of said distance are stored, and wherein said voltage generation means reads information about an optimum bias voltage from said memory based on information about the present value of the pressure inside the specimen chamber and on information about the present value of said distance and sets the potential of said specimen based on the information about the optimum bias voltage read out.

3. The low-vacuum scanning electron microscope of claim 2, wherein information about the present distance is derived from one of information about the height of the specimen stage on which said specimen holder is carried and information about an excitation current through said condenser lenses.

4. The low-vacuum scanning electron microscope of claim 1, wherein said voltage generation means sets the potential of said specimen by applying a voltage to said specimen holder.

5. A low-vacuum scanning electron microscope comprising:
   an electron gun for producing and accelerating an electron beam;
   condenser lenses for focusing said electron beam onto a specimen placed within a specimen chamber in a low vacuum, said specimen being at a distance from said condenser lenses;
   scanning means for scanning said electron beam over said specimen in two dimensions;
   an electrode placed above said specimen;
   voltage generation means for applying a voltage between said specimen and said electrode to accelerate secondary electrons toward said electrode, said secondary electrons being emitted from said specimen by electron beam irradiation;
   current detection means for detecting one of an electric current flowing through said specimen and an electric current flowing through a specimen holder holding said specimen thereon; and
   means for obtaining a scanned image of the specimen based on an output signal from said current detection means,
   wherein said voltage generation means controls the voltage applied between said specimen and said electrode to promote an avalanche effect based on information about pressure inside said specimen chamber and on information about the distance between said specimen and said condenser lenses.

6. The low-vacuum scanning electron microscope of claim 5, wherein there is further provided a memory in which multiple values of optimum bias voltage corresponding to multiple values of the pressure inside the specimen chamber and multiple values of said distance are stored, and wherein said voltage generation means reads information about an optimum bias voltage from said memory based on information about the present value of pressure inside the specimen chamber and on information about the present value of said distance and sets the potential of said specimen based on the information about the optimum bias voltage read out.

7. The low-vacuum scanning electron microscope of claim 6, wherein information about the present value of the distance is derived from one of information about the height of the specimen stage on which said specimen holder is carried and information about an excitation current through said condenser lenses.

8. The low-vacuum scanning electron microscope of claim 5, wherein said electrode is an annular electrode.

9. The low-vacuum scanning electron microscope of any one of claims 1 to 8, wherein said specimen chamber has a low degree of vacuum of approximately 10 to 300 Pa.

* * * * *